United States Patent [19]

Rajoharison et al.

[11] Patent Number: 4,642,359

[45] Date of Patent: Feb. 10, 1987

[54] PROCESS FOR PREPARING PYRYLIUM SALTS

[75] Inventors: Harivelo G. Rajoharison; Christian M. Roussel, both of Marseilles, France

[73] Assignee: Eastman Kodak Company, Rochester, N.Y.

[21] Appl. No.: 755,658

[22] Filed: Dec. 10, 1984

Related U.S. Application Data

[63] Continuation of Ser. No. 497,471, May 23, 1983, abandoned.

[30] Foreign Application Priority Data

Jun. 8, 1982 [FR] France .................. 82 09928

[51] Int. Cl.$^4$ .......................................... C07D 309/32
[52] U.S. Cl. ..................................... 549/356; 549/427; 549/428; 546/348
[58] Field of Search ..................... 549/356, 427, 428

[56] References Cited

U.S. PATENT DOCUMENTS 4,221,722  9/1980  Arnaud et al. .................. 549/356

FOREIGN PATENT DOCUMENTS 1340971  9/1963  France .................. 549/356

OTHER PUBLICATIONS

Hammett et al., JACS 54, 2721, 1932.
Balaban et al., JCS, 1961, p. 3553.
Howells et al., Chem. Rev., 1977, p. 69.
Bascombe et al., J. Chem. Soc., 1096, (1959).
Grondin et al., Bull. Soc. Chim., France, 1779, (1976).
Gillespie et al., JACS, 95, 5173, (1973).
Gillespie et al., JACS, 93, 5083, (1971).
C. H. Rochester, "Acidity Functions", Academic Press, New York, 1970, pp. 26, 50.

Primary Examiner—Nicky Chan
Attorney, Agent, or Firm—Arthur H. Rosenstein

[57] ABSTRACT

A process for selectively preparing isomers of polysubstituted pyrylium salts from isoolefins or isoolefin precursors comprises diacylating the isoolefin or isoolefin precursor with a carboxylic acid anhydride in the presence of an acid having a Hammett acidity function, at about 22°-25° C. when pure, between −10 and −5. This method is selective to obtain the most substituted isomer of pyrylium salt that can be obtained from the isoolefin or isoolefin precursor.

20 Claims, No Drawings

4,642,359

PROCESS FOR PREPARING PYRYLIUM SALTS

This is a continuation of application Ser. No. 497,471, filed May 23, 1983, now abandoned.

FIELD OF THE INVENTION

This invention relates to a process for selectively preparing isomers of polysubstituted pyrylium salts from isoolefins or isoolefin precursors comprising diacylating the isoolefin or isoolefin precursor with a carboxylic acid anhydride in the presence of an acid catalyst having a Hammett acidity function, when pure, between $-10$ and $-5$.

BACKGROUND OF THE INVENTION

Pyrylium salts are of great use, especially as intermediates in organic synthesis for materials such as phenols, vitamin precursors such as vitamin E, pyridines and anilines.

Applications of pyrylium salts have been recently reviewed by A. T. Balaban et al in *Advances in Heterocyclic Chemistry,* Suppl. 2, Academic Press, N.Y., 1982.

The conventional method for preparing pyrylium salts having substituents in the 2 and 6 positions comprises diacylating alkenes or alkene precursors such as tertiary alkyl halides or secondary or tertiary alkyl alcohols in the presence of Lewis acids or strong protonic acids such as perchloric acid or trifluoromethane sulfonic acid with the aid of acid anhydrides or acid halides as acylating agents.

In A. T. Balaban and C. D. Nenitzescu (Journal of Chemical Society, 1961, page 3553) the diacylation of 2-methyl-2-butene with acetic anhydride or acetyl chloride and a strong acid such as perchloric acid or sulfuric acid to achieve a mixture of 2,3,4,6-tetramethylpyrylium salt and 4-ethyl-2,6-dimethylpyrylium salt is described. The proportion of the more substituted isomer (2,3,4,6-tetramethylpyrylium salt) was only about 80%.

In R. D. Howells and J. D. McCown (Chemical Reviews, February 1977, page 69) pyrylium salts were prepared using trifluoromethane sulfonic acid as an acylation catalyst.

In the above prior art processes the selectivity of obtaining the most substituted isomer is undesirably low. A mixture of isomers is obtained, said mixture being difficult to purify. In the above processes wherein perchloric acid is used as an acid catalyst, pyrylium perchlorates are formed. These materials are particularly unstable and are very difficult to store and handle.

There has been a need to obtain a process having a high specificity for preparing the most highly substituted pyrylium salts in high yields. The need of such a process is particularly noted in the synthesis of substituted phenols, pyridines and anilines with substitution patterns not otherwise obtainable.

SUMMARY OF THE INVENTION

According to the present invention, the most substituted pyrylium salt isomers are selectively obtained by diacylating a substituted isoolefin optionally generated in situ from an isoolefin precursor, the latter having at least 5 carbon atoms including a tertiary carbon atom bearing at least one methyl substituent and at least one substituted methylene. The diacylation is performed with a carboxylic acid anhydride in the presence of an acid having a Hammett acidity function (Ho), at about $22°-25°$ C. when pure, between $-10$ and $-5$. A good yield of stable salts is obtained.

The acidity function Ho (Hammett et al JACS 54, 2721, 1932) is a measurement of the tendency of an acid to transfer a proton to a reference molecule which is a basic indicator. The Ho is independent of the basic indicator used.

The following table gives the values of Ho at about $22°-25°$ C. for a few pure acids:

| Acid | Ho |
| --- | --- |
| $CH_3SO_3H$ | $-7.9$ |
| $CF_3SO_3H$ | $-14.1$ |
| $HClO_4$ anhydrous | $-11.9$ to $-12.3$ |
| $H_2SO_4$ 100% | $-11.93$ |
| $FSO_3H$ | $-15.07$ |
| $CH_3CHCO_2H$<br>\|<br>$SO_3H$ | $-5$ to $-10$<br>(estimated) |

PREFERRED EMBODIMENTS OF THE INVENTION

Examples of acid catalysts useful herein include alkanesulfonic acids such as methanesulfonic acid, ethanesulfonic acid and propanesulfonic acid, α-sulfocarboxylic acids prepared from sulfuric acid and carboxylic acid anhydride such as α-sulfoacetic acid, α-sulfo fatty acids prepared from sulfur trioxide and fatty acids such as α-sulfopalmitic acid, α-sulfostearic acid and α-sulfomyristic acids, phosphoric acid and aryl sulfonic acids such as p-toluenesulfonic acid, benzenesulfonic acid and naphthalenesulfonic acid.

Alpha-sulfocarboxylic acid is prepared from appropriate amounts of sulfuric acid and carboxylic acid anhydride and can be prepared in situ. However, the preparation should occur before the addition of isoolefin or isoolefin precursor. No sulfuric acid should remain when the isoolefin precursor is added.

The isoolefin or isoolefin precursor contains at least 5 carbon atoms including a tertiary carbon atom bearing at least one methyl substituent and at least one substituent which is a substituted methylene group. The methylene group can be substituted by alkyl, aryl or aralkyl groups possibly substituted by groups such as alkoxy such as methoxy, hydroxy, carboxy, sulfo and halogen such as chloride.

Preferably, the substituted isoolefin in protonated form, or the isoolefin precursor in ionized form has the structure:

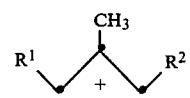

wherein $R^1$ is hydrogen, alkyl or aryl such as methyl, ethyl or phenyl and $R^2$ is alkyl or aryl and at least one of $R^1$ and $R^2$ is alkyl or aryl which can be substituted with a member of the group consisting of alkoxy, halogen, carboxy, sulfo and hydroxy.

Examples of useful isoolefins include 2-methyl-1-butene, 2-methyl-2-butene, 2-methyl-1-pentene, 2-methyl-2-pentene, 3-methyl-2-pentene, 2-ethyl-1-butene and citronellol.

An isoolefin precursor is a compound capable of providing a carbocation in the presence of an acid.

Examples of these include alcohols, esters, ethers and halides. In a preferred embodiment, the isoolefin precursor is a tertiary alcohol. Preferred alcohols contain at least 5 carbon atoms, such as 2-methyl-2-pentanol, 3-methyl-3-pentanol, 2-methyl-2-butanol, 2,4-dimethyl-2-pentanol and 2-methyl-1-phenyl-2-propanol.

Examples of carboxylic acid anhydrides useful herein include acetic acid anhydride, propionic anhydride, butyric anyhydride and benzoic acid anhydride.

Generally, the molar ratio of carboxylic acid anhydride to the acid having a Hammett acidity function when pure between $-10$ and $-5$ is between about 1:1 to 8:1. The molar ratio of the weak acid to the isoolefin or isoolefin precursors is preferably from about 1:1 to 5:1. If α-sulfocarboxylic acid is to be formed in situ, the amount of carboxylic acid anhydride used should be enough to allow the diacylation as well as to form the α-sulfocarboxylic acid. Generally, however, the α-sulfocarboxylic acids are prepared in a separate step by heating the stirred mixture of sulfuric acid and the carboxylic acid anhydride at 80° C. for about 30 minutes.

The acylation reaction is carried out at a temperature in the range from 60° C. to 100° C. for a time from 1 hour to 3 hours, and preferably at 80° C. for 2 hours.

The excess of carboxylic acid anhydride is then hydrolyzed or distilled, ethyl ether is added and the pyrylium salts are extracted in the aqueous phase.

The pyrylium salts obtained according to the invention are preferably isolated and analyzed after complete evaporation of the aqueous phase, or preferentially characterized by transformation into corresponding pyridines (by treatment of their aqueous solution with concentrated ammonium hydroxide (34%) and extraction in an organic solvent).

This reaction is quantitative. The resulting mixture of pyridines is weighed for calculating the yield and analyzed by NMR[1]-H. The distribution of the isomers is calculated by gas chromatography.

The following chemical reaction is, for instance, believed to take place according to the process of the invention:

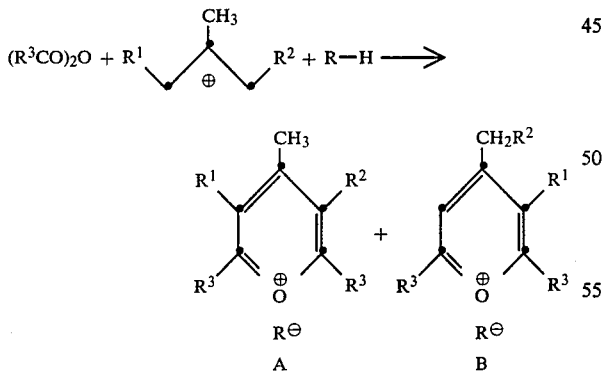

wherein $R^1$ is a hydrogen atom, an alkyl group preferably of from 1 to 30 carbon atoms or an aryl group;

$R^2$ is an alkyl group preferably of from 1 to about 30 carbon atoms or an aryl group wherein at least one of $R^1$ and $R^2$ is alkyl, aryl or aralkyl substituted or not by hydroxy, carboxy, alkoxy, sulfo or halogen groups;

$R^3$ is an alkyl group preferably of from 1 to 22 carbon atoms such as methyl, ethyl or propyl, or an aryl group such as phenyl;

RH represents the acid catalyst of Ho comprised between $-10$ and $-5$ as defined above.

Isomer A is preferentially formed. With the acids of Ho comprised between $-10$ and $-5$ according to the invention, the selectivity in isomer A may be increased up to 98-99% and is in all cases far better than that obtained by using the strong acids of the prior art, as will be shown hereafter in the comparative examples 1-c, 1-d, 2-c, 3-c, 4-b, 5-b and 6-b. With the acids of Ho comprised between $-10$ and $-5$ according to the invention, the selectivity in isomer A increased up to 98% to 99%.

It has been found that the higher the Ho of the acid, the better the selectivity.

It is noted that the above process is carried out in batch or continuous operations.

The following examples illustrate the invention.

In all the examples, a flask is used which is fitted with a condenser and a dropping funnel and is placed in a thermoregulated oil bath on a magnetic stirrer. The reaction mixture is protected from atmospheric moisture. The condenser and the dropping funnel are provided with calcium chloride tubes and the flask is swept with a light flow of nitrogen dried on sulfuric acid.

EXAMPLE 1

Diacylation of 2-methyl-2-butanol

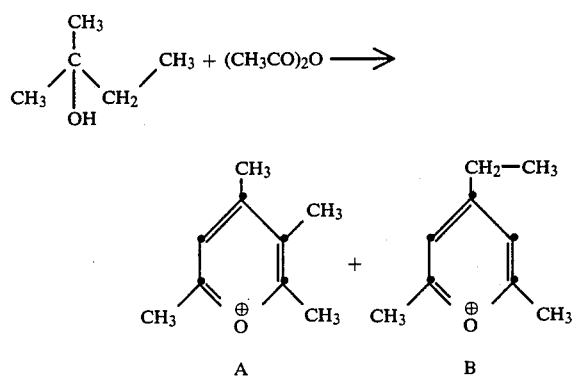

1-a.—Catalysis by methanesulfonic acid

To the mixture of 5.4 ml (0.05 mole) of 2-methyl-2-butanol and 57 ml (0.6 mole) of acetic anhydride, were rapidly added (in 3 to 5 mn) with stirring 6.6 ml (0.1 mole) of methanesulfonic acid. The reaction medium was then heated at 80° C. for 2 hours.

The reaction medium was cooled down to room temperature (ice-water bath), then it was slowly hydrolyzed with 25 ml of water to destroy the excess of acetic anhydride so that the temperature was kept from 35° C. to 40° C. One hundred ml of ethyl ether were added. After decantation, the organic phase was washed twice with 25 ml of water, and the aqueous phases were collected together and washed with 25 ml of ethyl ether. The resulting aqueous phase contained the mixture of isomeric pyrylium salts.

The quantitative transformation of the pyrylium salts into corresponding pyridines was achieved by adding the aqueous phase on 200 ml of ammonium hydroxide (34%) for about 30 mn with stirring. Pyridines were extracted by dichloromethane. After evaporation of the solvent, 4 g of the mixture of tetramethyl-2,3,4,6-pyridine and dimethyl-2,6-ethyl-4-pyridine (global yield:

59%) with a 98% content of tetramethyl-2,3,4,6-pyridine were obtained.

1-a'.

By the same method, but using 9.9 ml (0.15 mole) of methane sulfonic acid and by carrying out the reaction at 100° C. for 1 hour, a global yield in pyridines of 87% was obtained, with 98% of 2,3,4,6-tetramethylpyridine.

1-b.—Catalysis by sulfoacetic acid 5.6 ml (0.1 mole) of 96% sulfuric acid were mixed with stirring with 28.3 ml (0.3 mole) of acetic anhydride, then treated at 80° C. for 30 mn. 5.4 ml (0.05 mole of 2-methyl-2-butanol in 39.7 ml (0.42 mole) of acetic anhydride were then added so as to keep the temperature at 80°-85° C. The reaction was continued for 2 hours at 80° C.

After cooling, the reaction medium was treated as in Example 1-a. 6.35 g (global yield: 94%) of the mixture of pyridines was obtained, with a 96% content of 2,3,4,6-tetramethylpyridine.

1-c.—Catalysis by perchloric acid (comparative example)

A stirred mixture of 5.4 ml (0.05 mole) of 2-methyl-2-butanol and 76 ml (0.72 mole) of acetic anhydride was cooled to −10° C., then 8.6 ml (0.1 mole) of 70% perchloric acid were added so as to keep the temperature of the reaction medium between −5° C. and 0° C. The mixture was then heated at 80° C. for 2 hours.

After cooling, the reaction medium was treated as in Example 1-a.

6.1 g (global yield: 90%) of the mixture of pyridines were obtained, with a 90% content of 2,3,4,6-tetramethylpyridine.

1-d.—Catalysis by trifluoromethanesulfonic acid (comparative example)

The procedure of Example 1-a was repeated, adding 0.1 mole of trifluoromethanesulfonic acid to a mixture of 0.05 mole of 2-methyl-2-butanol and 0.6 mole of acetic anhydride.

The addition was controlled by cooling the mixture so as to keep the temperature at 60° C. during the addition of the acid.

6.4 g of the mixture of pyridines were obtained (global yield: 95%) with a 92% content of 2,3,4,6-tetramethylpyridine.

EXAMPLE 2

Dipropionylation of 2-methyl-2-butanol

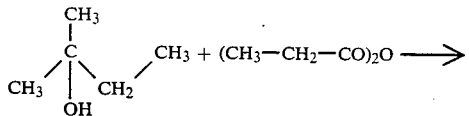

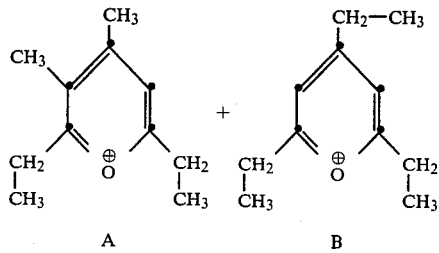

2-a.—Catalysis by methanesulfonic acid

The procedure of Example 1-a was repeated for this synthesis. From 0.05 mole (5.4 ml) of 2-methyl-2-butanol, 0.1 mole (6.5 ml) of methanesulfonic acid and 0.4 mole of propionic anhydride, after treating with NH$_4$OH the aqueous solution of pyrylium salts, 4.1 g (50%) were obtained of a mixture of 2,6-diethyl-3,4-dimethylpyridine and of 2,4,6-triethylpyridine in the respective proportions of 96% and 4%.

2-a'.

By the same procedure, but using 0.15 mole (9.9 ml) of methanesulfonic acid, and the operation being conducted at 100° C. for 1 hour, 6.2 g (76%) of pyridine containing mixture were obtained after treatments, with a 95% content of 2,6-diethyl-3,4-dimethylpyridine.

2-b.—Catalysis of α-sulfopropionic acid

The procedure of Example 1-b used in diacylation was repeated, using sulfuric acid and propionic anhydride as an α-sulfopropionic acid precursor.

From 0.05 mole (5.4 ml) of 2-methyl-2-butanol, 0.05 mole (2.8 ml) of 96% sulfuric acid and 0.66 mole (85 ml) of propionic anhydride, 4.3 g (53%) of pyridine mixture were obtained in the respective proportions of 96% and 4%, after treatment of the aqueous phase with NH$_4$OH.

The RMN$^1$-H analysis of the pyrylium salts shows that the stabilizing ion is α-sulfopropionate.

2-c.—Catalysis by perchloric acid (comparative example)

The procedure of Example 1-c was repeated. From 0.025 mole (2.7 ml) of 2-methyl-2-butanol, 0.05 mole (4.3 ml) of 70% perchloric acid and 0.32 mole (42 ml) of propionic anhydride, 3.2 g (79%) of the pyridine mixture were obtained in the respective proportions of 65% and 35%, after treatment of the aqueous solution of pyrylium salts with NH$_4$OH.

EXAMPLE 3

Dibutylation of 2-methyl-2-butanol

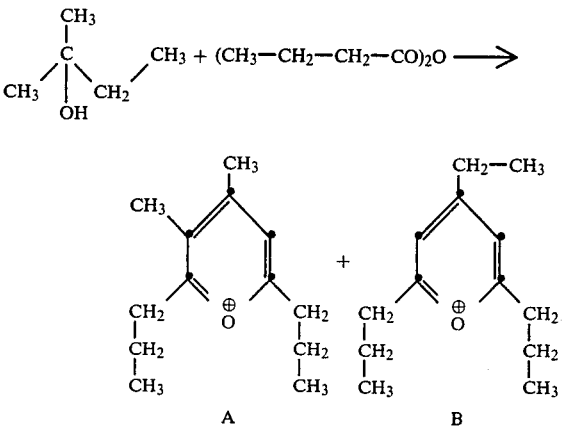

3-a.—Catalysis by methanesulfonic acid

The procedure of Example 1-a was repeated. From 0.025 mole (2.7 ml) of 2-methyl-2-butanol, 0.05 mole (3.3 ml) of methanesulfonic acid and 0.3 mole (49 ml) of butyric anhydride, 1.6 g (34%) was obtained of a mixture of 3,4-dimethyl-2,6-di-n-propylpyridine and 4-ethyl-2,6-di-n-propylpyridine, in the respective proportions of 96% and 4%.

3-b.—Catalysis by α-sulfobutyric acid

As in Example 2-b, the procedure of Example 1-b was repeated. From 0.05 mole (5.4 ml) of 2-methyl-2-butanol, 0.05 mole (2.8 ml) of 96% sulfuric acid and 0.66 mole (108 ml) of butyric anhydride, 4.1 g (43%) of pyridine mixtures were obtained, in the respective proportions of 97% and 3%, after treatment and transformation of the pyrylium salts.

The NMR[1]-H analysis of the pyrylium salts showed that the ion stabilizing them is the ion α-sulfobutyrate

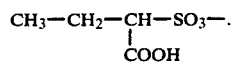

butyric anhydride, 1.5 g (16%) of pyridine mixture was obtained, in the respective proportions of 75% and 25%.

The results of Examples 1, 2 and 3 are shown in Table I. Table II gives the characteristics of the pyrylium salts obtained, and Table III those of the corresponding pyridines.

TABLE I

| Examples | Anhydride | Mole | Catalyst | Mole | Global yield in pyridines | Yield in isomer A |
|---|---|---|---|---|---|---|
| 1-a | acetic | 0.6 | $CH_3SO_3H$ | 0.1 | 59% | 98% |
| 1-a' | acetic | 0.6 | $CH_3SO_3H$ | 0.15 | 87% | 98% |
| 1-b | acetic | 0.72 | $HO_2CCH_2SO_3H$ | 0.1 | 94% | 96% |
| 1-c (comparative) | acetic | 0.72 | $HClO_4$ | 0.1 | 90% | 90% |
| 1-d (comparative) | acetic | 0.6 | $CF_3SO_3H$ | 0.1 | 95% | 92% |
| 2-a | propionic | 0.4 | $CH_3SO_3H$ | 0.1 | 50% | 96% |
| 2-a' | propionic | 0.6 | $CH_3SO_3H$ | 0.15 | 76% | 95% |
| 2-b | propionic | 0.6 | $CH_3CH(COOH)SO_3H$ | 0.05 | 53% | 96% |
| 2-c (comparative) | propionic | 0.64 | $HClO_4$ | 0.1 | 79% | 65% |
| 3-a | butyric | 0.6 | $CH_3SO_3H$ | 0.1 | 34% | 96% |
| 3-b | butyric | 0.66 | $CH_3CH_2CH(COOH)SO_3H$ | 0.05 | 43% | 97% |
| 3-c (comparative) | butyric | 0.72 | $HClO_4$ | 0.05 | 16% | 76% |

TABLE II

CHARACTERISTICS OF THE PYRYLIUM SALTS
Analyses $RMN^1H$ [Solvent: $CF_3COOH/CDCl_3$ (80:20) unless otherwise stated VARIAN A 360]

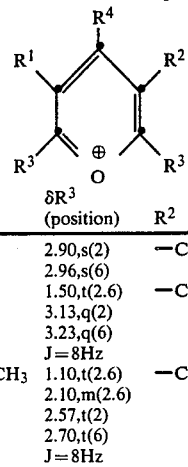

| Example | Pyrylium | $R^3$ | $\delta R^3$ (position) | $R^2$ | $\delta R^2$ | $R^4$ | $\delta R^4$ | $R^1$ | $\delta R^1$ |
|---|---|---|---|---|---|---|---|---|---|
| 1 | 2,3,4,6-tetra-methylpyrylium | —$CH_3$ | 2.90,s(2) 2.96,s(6) | —$CH_3$ | 2.46,s | —$CH_3$ | 2.76,s | —H | 7.70,s |
| 2 | 2,6-diethyl-3,4-dimethylpyrylium* | —$CH_2CH_3$ | 1.50,t(2.6) 3.13,q(2) 3.23,q(6) J=8Hz | —$CH_3$ | 2.43,s | —$CH_3$ | 2.70,s | —H | 7.63,s |
| 3 | 3,4-dimethyl-2,6-di-n-propyl-pyrylium* | —$CH_2CH_2CH_3$ | 1.10,t(2.6) 2.10,m(2.6) 2.57,t(2) 2.70,t(6) J=8Hz | —$CH_3$ | 2.43,s | —$CH_3$ | 2.70,s | —H | 7.63,s |

*solvent = $CF_3COOH/CCl_4$ (80:20)
The chemical displacements of the counter-ions are the following:
For the compound of Example 1
$CH_3SO_3^\ominus$    3.31 ppm,s $HO_2CCH_2SO_3^\ominus$ 4.48 ppm,s
For the compound of Example 2
$CH_3$—CH(COOH)—$SO_3^\ominus$  1.66 ppm,d et 4.23 ppm,q (J=7Hz)

For the compound of Example 3
$CH_3$—$CH_2$—CH(COOH)—$SO_3^\ominus$  1.10 ppm,t 2.10 ppm,m et 4.03 ppm,t(J=7Hz)

3-c.—Catalysis by perchloric acid (comparative example)

The procedure of Example 1-c was repeated: From 0.05 mole (5.4 ml) of 2-methyl-2-butanol, 0.05 mole (4.3 ml) of 70% perchloric acid and 0.72 mole (58.5 ml) of

TABLE III

CHARACTERISTICS OF THE PYRIDINES OBTAINED

Example 1
2,3,4,6-tetramethylpyridine: $RMN^1$—H ($CDCl_3$): 2.15 (3H,s),

TABLE III-continued
CHARACTERISTICS OF THE PYRIDINES OBTAINED 2.22 (3H,s), 2.44 (3H,s), 2.48 (3H,s), 6.78 (1H,s); Eb: 86–88° C. 18 mm Hg colorless oil
4-ethyl-2,6-dimethylpyridine: RMN[1]H (CDCl$_3$): 1.20 (3H,t), 2.48 (6H,s), 2.54 (2H,q), 6.78 (2H,s); colorless oil
Example 2
2,6-diethyl-3,4-dimethylpyridine: RMN[1]—H (CCl$_4$): 1.20 (6H,t), 2.06 (3H,s), 2.12 (3H,s), 2.62 (2H,q), 2.73 (2H,q), 6.60 (1H,s); colorless oil
2,4,6-triethylpyridine: RMN[1]—H (CCl$_4$): 1.20 (3H,t), 1.23 (6H,t), 2.56 (2H,q), 2.70 (4H,q) 6.65 (2H,s); colorless oil
Example 3
3,4-dimethyl-2,6-di-n-propylpyridine: RMN[1]—H (CDCl$_3$): 0.93 (3H,t), 0.97 (3H,t), 1.70 (4H,m), 2.10 (3H,s), 2.13 (3H,s), 2.63 (2H,t), 2.77 (2H,t), 6.67 (1H,s); colorless oil
4-ethyl-2,6-di-n-propylpyridine: RMN[1]—H (CDCl$_3$): 0.93 (6H,t), 1.20 (2H,t), 1.70 (4H,m), 2.70 (2H,q et 4H,t), 6.70 (2H,s); colorless oil

EXAMPLE 4
Diacylation of 3-methyl-3-pentanol

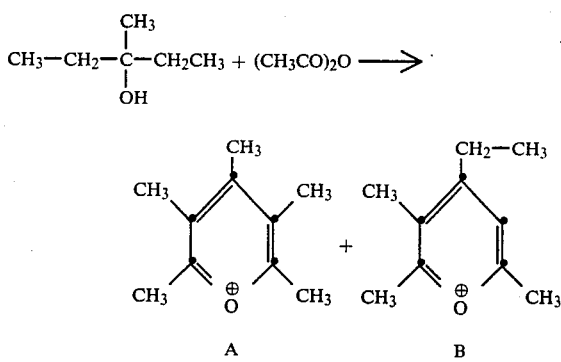

4-a.—Catalysis by methanesulfonic acid

To a stirred mixture of 57 ml (61.2 g, 0.6 mole) of acetic anhydride and 6.2 ml (5.1 g, 0.05 mole) of 3-methyl-3-pentanol were rapidly added in 3–5 mn, 9.9 ml (14.7 g, 0.15 mole) of methanesulfonic acid. During the addition, the temperature of the mixture evolved from 25° C. to 50° C. The reaction mixture was then heated at 100° C. for 1 hour.

After cooling, hydrolysis and usual treatments of the various phases, an aqueous phase (A) was obtained containing the pentamethylpyrylium and 4-ethyl-b 2,3,6-trimethylpyrylium salts.

The reaction of the phase (A) with 200 ml of 34% NH$_4$OH, the extraction of the products by dichloromethane and the evaporation of the latter permitted to obtain 6.9 g (93%) of a mixture of pentamethylpyridine and 4-ethyl-2,3,4,6-trimethylpyridine in the respective proportions of 87% and 13%.

4-b.—Catalysis by perchloric acid (comparative example)

The reaction using perchloric acid (49%) as a catalyst led to a global yield in pyridines of 95%, with a distribution of 65% and 35% respectively.

Characteristics of the pyridines obtained: Pentamethylpyridine: NMR[1]-H (CDCl$_3$): 2.16 (9H,s) 2.46 (6H,s)
4-ethyl-2,3,6-trimethylpyridine: NMR[1]-H (CDCl$_3$): 1.16, 2.16 (3H,s), 2.46 (6H,s), 2.56 (2H,q), 6.76 (1H,s); colorless oil.

Table IV gives the characteristics of the pentamethylpyrylium salt.

EXAMPLE 5
Diacylation of 2-methyl-2-pentanol

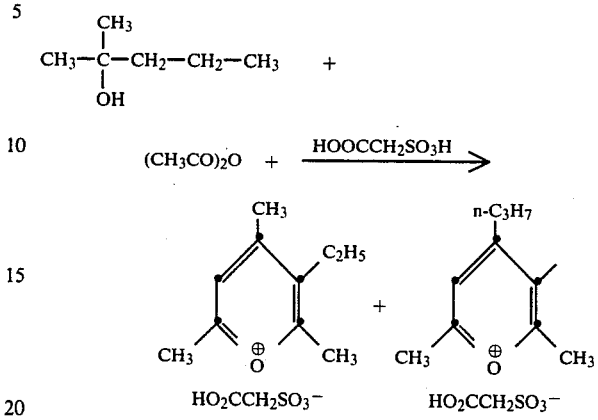

5-a.—Catalysis by α-sulfoacetic acid

To 55 ml (59.4 g, 0.58 mole) of acetic anhydride, were rapidly added 2.8 ml (0.065 mole) of 96% sulfuric acid. The mixture was then heated at 80° C. for 2 hours during which the solution progressively assumed a brown red color. It was then cooled to 60° C. then 5.1 g (0.05 mole) of 2-methyl-2-pentanol were added. After further reacting at 60° C. for 4 hours, the mixture was cooled to room temperature then 100 ml of ethyl ether were added. A black lower phase was separated from the brighter ethereal phase. The latter was washed twice with 25 ml H$_2$O and the aqueous phases were collected together with the black solution (miscible in water, non-miscible in ethyl ether and containing the pyrylium salts), then washed with 25 ml of ether. The resulting aqueous phase contained the 3-ethyl-2,4,6-trimethylpyrylium and 2,6-dimethyl-4-n-propyl-pyrylium salts.

Transformation into pyridines was carried out as previously and permitted to obtain 4.7 g (63%) of a mixture of 3-ethyl-2,4,6-trimethylpyridine and 2,6-dimethyl-4-n-propyl in the respective proportions of 94% and 6%.

5-b.—Catalysis by perchloric acid (comparative example)

In a reaction catalyzed by perchloric acid, a global yield in pyridines of 71% was obtained, with a distribution of 71% and 29% respectively.

Characteristics of the pyridines obtained:
3-ethyl-2,4,6-trimethylpyridine: NMR[1]-H (CDCl$_3$): 1.06 (3H,t) 2.23 (3H,s), 2.50 (6H,s), 2.56 (2H,q), 6.70 (1H,l): colorless oil.
2,6-dimethyl-4-n-propylpyridine: NMR[1]-H (CDCl$_3$): 0.90 (3H,t), 1.56 (2H,m), 2.40 (6H,s and 2H,t), 6.70 (2H,s): colorless oil.

Table IV gives the characteristics of the 3-ethyl-2,4,6-trimethylpyrylium.

EXAMPLE 6
Diacylation of 2,4-dimethyl-2-pentanol

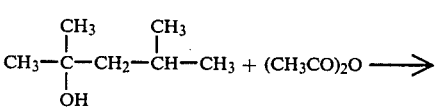

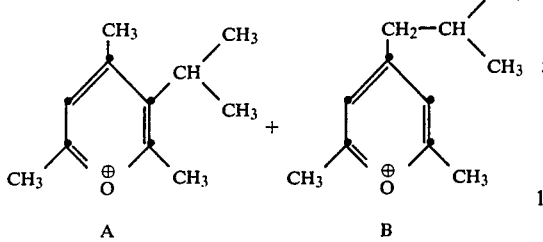

6-a.—Catalysis by sulfoacetic acid 5.6 ml (0.1 mole) of 96% sulfuric acid were mixed with stirring with 28.3 ml (0.3 mole) of acetic anhydride then heated at 80° C. for 30 mn. Then 5.8 g (0.05 mole) of 2,4-dimethyl-2-pentanol in 39.7 ml (0.42 mole) of acetic anhydride were added so as to keep the temperature at 80°-85° C. The reaction was continued for 2 hours at 80° C.

After cooling to room temperature and hydrolysis with 25 ml of water, 100 ml of ethyl ether were added. The aqueous phase was decanted and the organic phase was washed twice with 25 ml of water. The aqueous phases were collected together and washed with 25 ml of ether. The resulting aqueous phase contained the above pyrylium salts. The characteristics of isomer A are given in Table IV.

The reaction of the aqueous phase on a stirred solution of 200 ml of 34% NH$_4$OH permitted to obtain 6.2 g (76%) of a mixture of 3-isopropyl-2,4,6-trimethylpyridine and 2,6-dimethyl-4-isobutylpyridine in the respective proportions of 83% and 17%.

6-b.—Catalysis by perchloric acid (comparative example)

To the mixture of 2.9 g (0.025 mole) of 2,4-dimethyl-2-pentanol and 34 ml (0.36 mole) of acetic anhydride were added 2.2 ml (0.026 mole) of 70% perchloric acid so as to keep the temperature of the mixture between −5° C. and 0° C. The mixture was then heated at 80° C. for 2 hours.

After the usual treatments of the reaction medium and transformation of the mixture of the above pyridines, 3.3 g (80%) of the mixture of the above pyridines were obtained in the respective proportions of 75% and 25%.

EXAMPLE 7

Diacylation of 3,7-dimethyl-6-octene-1-ol-1 (Citronellol)

In a 500 ml flask fitted with a mechanical stirrer, a dropping funnel, a thermometer and a condenser, 5.6 ml (0.1 mole) of 96% sulfuric acid were rapidly added to 110 ml (1.2 mole) of acetic anhydride, to raise the temperature to 80° C. and to keep it during 30 mn. 18.6 ml (0.1 mole) of citronellol were added dropwise for two hours. The reaction medium was then kept at 80° C. for 4 hours.

At the end of the reaction, the reaction mixture was cooled down to room temperature, and hydrolyzed with 140 ml of water. After adding 200 ml of ether, the aqueous phase was decanted, and the organic phase was washed twice with 40 ml of water. The aqueous phase was washed twice with 70 ml of ether. A homogeneous solution of pyrylium salts A and B below was obtained.

After treatment with ammonium hydroxide, extraction by dichloromethane and evaporation of this solvent, 21.8 g (83%) of a mixture of 5-(2,4,6-trimethyl-3-pyridyl)-3-methyl-pentyl acetate and 6-(2,6-dimethyl-3-pyridyl)-3-methyl-hexyl acetate were obtained. NMR[1]-H analysis show that isomer B was present in the mixture in an amount of less than 5%.

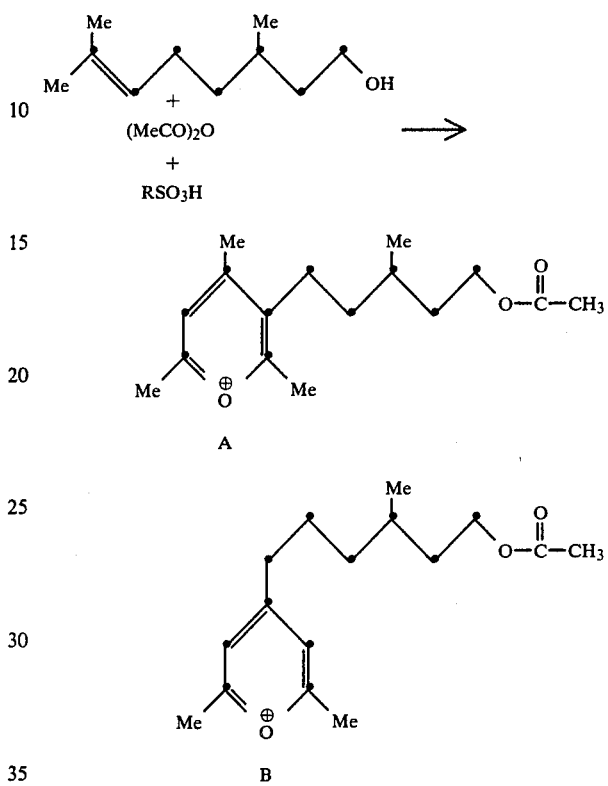

5-(2,4,6-trimethyl-3-pyridyl)-3-methyl-pentyl acetate: NMR[1]-H (CDCl$_3$): 1.05 (3H,d), 1.50 (4H,m), 2.05 (3H,s), 2.45 (3H,s), 2.55 (2H,t), 4.15 (2H,t), 6.75 (1H,s), Boiling point: 169° C./4 mm Hg: colorless oil.

EXAMPLE 8

Diacylation of 2-methyl-1-phenyl-2-propanol

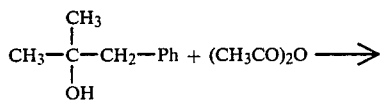

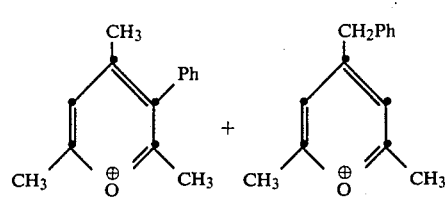

Catalysis by sulfoacetic acid 39 ml (0.33 mole) of 98% sulfuric acid are mixed with stirring with 94 ml (1 mole) of acetic anhydride then heated at 80° C. for 30 minutes. Then 50 ml (0.33 mole) of 2-methyl-1-phenyl-2-propanol in 276 ml (2.9 mole) of acetic anhydride were added so as to keep the temperature at 80°-85° C. The reaction was continued for 2 hours at 80° C. An aqueous solution containing the above pyrylium salts was obtained.

The reaction of the aqueous phase on a stirred solution of excess 34% NH$_4$OH resulted in 24.5 g (38%) of a mixture of 3-phenyl-2,4,6-trimethylpyridine and 4-benzyl-2,6-dimethylpyridine in the respective proportion of 96% and 4%.

Characteristics of 3-phenyl-2,4,6-trimethylpyridine obtained NMR[1]-H (CDCl$_3$): 1.97 (3H,s), 2.23 (3H,s), 2.50 (3H,s), 6.83 (1H,s), 7.20 (5H,m); pale yellow oil B.P. 117° C. (3 mm Hg).

TABLE IV

CHARACTERISTICS OF THE PYRYLIUM SALTS
NMR[1]—H analyses [Solvent: CF$_3$COOH/CDCl$_3$ (80:20) VARIAN A 360]

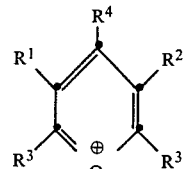

| Example | Pyrylium | R$^3$ | (position) | R$^2$ | δR$^2$ | R$^4$ | δR$^4$ | R$^1$ | δR$^1$ |
|---|---|---|---|---|---|---|---|---|---|
| 4 | pentamethyl pyrylium | —CH$_3$ | 2.96,s(2,6) | —CH$_3$ | 2.55,s | —CH$_3$ | 2.75,s | —CH$_3$ | 2.55,s |
| 5 | 3-ethyl-2,4,6-trimethyl-pyrylium | —CH$_3$ | 2.90,s(2) 2.96,s(6) | —CH$_2$—CH$_3$ | 1.30,t 2.90,q | —CH$_3$ | 2.76,s | —H | 7.70,s |
| 6 | 3-isopropyl-2,4,6-trimethyl-pyrylium | —CH$_3$ | 2.86,s(2) 2.96,s(6) | —CH(CH$_3$)$_2$ | 1.46,d 3.53,m J=8Hz | —CH$_3$ | 2.80,s | —H | 7.67,s |
| 8 | 3-phenyl-2,4,6-tri-methylpyrylium | —CH$_3$ | 2.61,s(2) 2.93,s(6) | —C$_6$H$_5$ | 1.40,m | —CH$_3$ 2.43,s system AB at 8.61 ppm, J$_{AB}$=9Hz Δ$_{AB}$=49Hz | | —H | 1.80,s |

The chemical displacement of the counter-ion HO$_2$CCH$_2$SO$_3$$^-$ for the compounds of Examples 5, 6 and 8 is 4.48 ppm,s.

The invention has been described in detail with particular reference to preferred embodiments thereof, but it will be understood that variations and modifications can be effected within the spirit and scope of the invention.

What is claimed is:

1. A process for the preparation of the most substituted isomer of a polysubstituted pyrylium salt that can be obtained from an isoolefin or isoolefin precursor having at least 5 carbon atoms including a tertiary carbon atoms bearing at least 1 methyl substituent and 1 substituent which is substituted methylene, comprising diacylating said isoolefin or isoolefin precursor with a carboxylic acid anhydride in the presence of an acid having a Hammett acidity function, at about 22°-25° C. when pure, between −7.9 and −5.

2. The process of claim 1 wherein the isoolefin, in protonated form, or the isoolefin precursor in ionized form, has the structure:

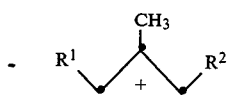

wherein R$^1$ is hydrogen, alkyl or aryl and R$^2$ is alkyl or aryl wherein at least one of R$^1$ and R$^2$ is alkyl, aryl or aralkyl substituted or note with a member of the group consisting of alkoxy, halogen, carboxy, sulfo and hydroxy.

3. The process of claim 1 wherein the acid is an alkane sulfonic acid.

4. The process of claim 3 wherein the alkane sulfonic acid is methane sulfonic acid.

5. The process of claim 1 wherein the acid is α-sulfocarboxylic acid.

6. The process of claim 1 wherein the acid is an aryl sulfonic acid.

7. The process of claim 1 wherein the molar ratio of the isoolefin or isoolefin precursor to acid is 1:1 to 1:5.

8. The process of claim 1 wherein the carboxylic acid anhydride is acetic anhydride.

9. The process of claim 1 wherein the carboxylic acid anhydride is propionic anhydride.

10. The process of claim 1 wherein the carboxylic acid anhydride is butyric anhydride.

11. The process of claim 1 wherein the carboxylic acid anhydride is benzoic anhydride.

12. The process of claim 1 wherein the molar ratio of carboxylic acid anhydride to the acid having a Hammett acidity function, when pure, between −7.9 and −5 is 1:1 to 8:1.

13. The process of claim 1 wherein the isoolefin is substituted with at least one methyl and at least one alkyl, aryl or aralkyl substituted with a member of the group consisting of alkoxy, hydroxy, carboxy, sulfo and hydroxy.

14. The process of claim 1 wherein the isoolefin precursor is a tertiary alcohol.

15. The process of claim 14 wherein the tertiary alcohol is 2-methyl-2-butanol.

16. The process of claim 14 wherein the tertiary alcohol is 3-methyl-3-pentanol.

17. The process of claim 14 wherein the tertiary alcohol is 2,4-dimethyl-2-pentanol.

18. The process of claim 14 wherein the tertiary alcohol is 2-methyl-1-phenyl-pentanol.

19. The process of claim 14 wherein the tertiary alcohol is citronellol.

20. A process for the preparation of the most substituted isomer of a polysubstituted pyrylium salt that can be obtained from an isoolefin or isoolefin precursor having at least 5 carbon atoms including a tertiary carbon atom bearing at least 1 methyl substituent and 1 substituent which is substituted methylene, comprising diacylating said isoolefin or isoolefin precursor with a carboxylic acid anhydride in the presence of an α-sulfocarboxylic acid.

* * * * *